United States Patent [19]

Mann et al.

[11] 4,231,027
[45] Oct. 28, 1980

[54] BATTERY MONITORING MEANS FOR AN IMPLANTABLE LIVING TISSUE STIMULATOR

[75] Inventors: Brian M. Mann, Northride; Russell R. Beane, Sepulveda, both of Calif.

[73] Assignee: Pacesetter Systems, Inc., Sylmar, Calif.

[21] Appl. No.: 16,200

[22] Filed: Feb. 28, 1979

[51] Int. Cl.³ .................. A61N 1/36; G08B 21/00; G01N 27/46
[52] U.S. Cl. .................. 340/636; 128/419 PT; 324/430
[58] Field of Search .......... 340/177 R, 636; 324/29.5; 128/419 PT, 419 PS

[56] References Cited

U.S. PATENT DOCUMENTS

| | | | |
|---|---|---|---|
| 3,680,072 | 7/1972 | Charbonnier et al. | 324/29.5 |
| 3,789,854 | 2/1974 | Lee | 128/419 PS |
| 4,026,305 | 5/1977 | Brownlee et al. | 128/419 PT |
| 4,080,560 | 3/1978 | Abert | 340/636 |
| 4,120,307 | 10/1978 | Jirak et al. | 128/419 PT |

Primary Examiner—Thomas A. Robinson
Attorney, Agent, or Firm—Freilich, Hornbaker, Wasserman, Rosen & Fernandez

[57] ABSTRACT

A battery monitoring means for an implantable living tissue stimulator system in which various battery voltages are telemetered to an external receiving means, these voltages being related to the internal impedance of the implanted battery. More specifically, a battery loading circuit is provided which incorporates a switch means for loading the battery in accordance with a predetermined sequence. In a specific embodiment, first and second resistors are sequentially connected across the battery. The battery output voltage is telemetered to an external receiving means during this sequential connection. By knowing the values of the two resistors, the internal impedance of the battery can be calculated, this impedance being related to the remaining life of the implanted battery.

6 Claims, 3 Drawing Figures

BATTERY MONITORING MEANS FOR AN IMPLANTABLE LIVING TISSUE STIMULATOR

FIELD OF THE INVENTION

The invention relates to battery monitoring systems for implantable tissue stimulators such as heart pacemakers.

BACKGROUND OF THE INVENTION

Implantable tissue stimulators such as implantable pacemakers conventionally use a battery as a power means for generating tissue stimulation pulses and operating any electronics and telemetry means contained therein. Although typical pacemaker batteries have a relatively long life, they do eventually require replacement. Such replacement requires removal of the pacemaker and its subsequent reimplantation, thereby causing the patient to incur an additional although minimal risk. Consequently, there has long been a need to determine the life remaining in a pacemaker battery so that it can be replaced at an optimum time, early replacement subjecting the patient to unnecessary risk and late replacement subjecting him to a possibility that his pacemaker will fail. Techniques for determining remaining battery life by loading the battery with predetermined loads, measuring the output voltages of the battery as the load is varied, calculating the internal impedance of the battery from the output voltage measurements, and predicting battery life remaining from the calculated internal impedance are well understood. However, these techniques have not heretofore been utilized in implantable pacemakers because of the complexity involved and the relatively long life of batteries utilized therein. The present invention provides a simple and reliable means for monitoring the life remaining in a pacemaker battery, thereby solving a long standing problem of determining when the battery should be replaced.

SUMMARY OF THE INVENTION

The invention provides a battery monitoring means for an implantable living tissue stimulator having a telemetry means for transmitting and receiving signals related to the operation of the tissue stimulator. The battery monitoring means comprises means for providing the battery output voltage to the telemetry means, a load means for altering current through the battery, and a means for connecting the load means to the battery. The connecting means is cycled in accordance with a predetermined sequence initiated by a telemetry operator. In a specific embodiment, the load means comprises first and second resistors each of which can be sequentially connected across the battery output terminals by a switch means. The switch means could comprise any type of electronic switch, one example being a plurality of FET switches. Changes in battery output voltage as a result of sequentially connecting the first and second load resistors across the battery output terminals provide a means for calculating the internal impedance of the battery. Comparing this internal impedance with predetermined impedance versus battery life remaining characteristics of the particular implanted battery type provides a means for determining when the battery should be replaced.

DETAILED DESCRIPTION

As required, a detailed illustrative embodiment of the invention is disclosed herein. This embodiment exemplifies the invention and is currently considered to be the best embodiment for such purposes. However, it is to be recognized that other means for altering current through the battery could be utilized. Accordingly, the specific embodiment disclosed is representative in providing a basis for the claims which define the scope of the present invention.

Figure 1:
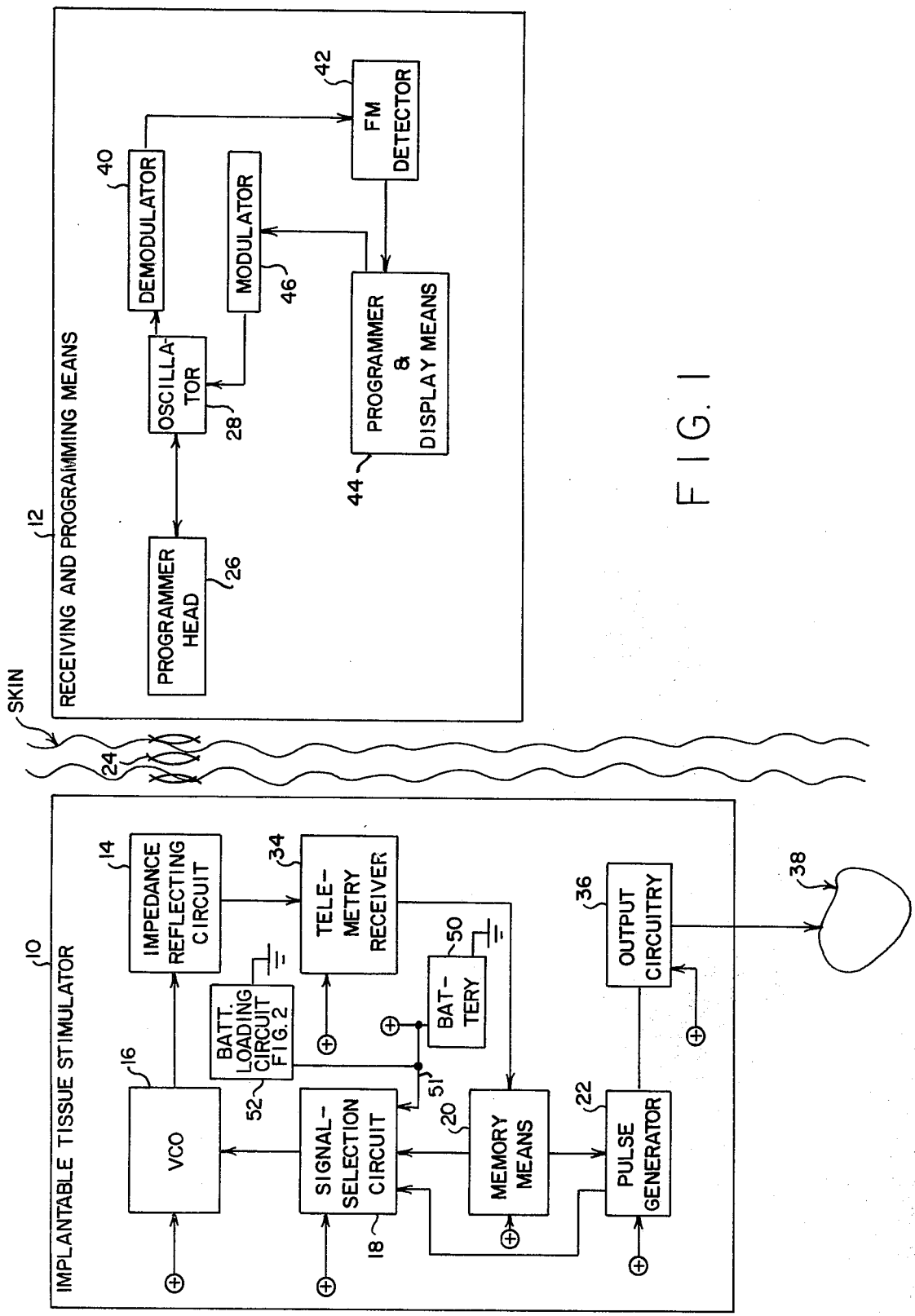
FIG. 1 is a block diagram of a living tissue stimulator system incorporating the battery monitoring means provided by the inventor.

A living tissue stimulator system incorporating a battery monitoring means provided by the invention is shown in FIG. 1. The human tissue stimulator system comprises an implantable tissue stimulator 10 and a receiving and programming means 12. The implantable tissue stimulator 10 could be a device generally known as a heart pacemaker. A telemetry means is included which comprises an impedance reflecting circuit 14 having an impedance related to an output voltage from a voltage control oscillator (VCO) 16 whose frequency is determined by an input signal to be telemetered. A signal selection circuit 18 receives input voltages from both a memory means 20 which provides digital inputs, and a pulse generator 22 which provides analog inputs. The signal selection circuit 18 includes means for selecting one of its input voltages to be telemetered, the selection being made in accordance with control signals from the memory means 20. The selected signal frequency modulates the VCO 16. The frequency modulated VCO 16 output signal then alters the impedance of the impedance reflecting circuit 14 which is magnetically coupled as schematically represented at 24 to a programmer head 26 which in turn is coupled to an oscillator 28. The output of the oscillator 28 is determined by the combined impedance of the programmer head 26 and the impedance of the impedance reflecting circuit 14 which is coupled to the programmer head 26. Thus, the oscillator 28 output is an FM modulated signal if the coupled impedance is reactive, and an AM modulated signal if the coupled impedance is resistive. In both cases the modulation on the oscillator 28 output is related to the output of the VCO 16 which is FM modulated by the signal to be telemetered.

The implantable tissue stimulator 10 also includes a telemetry receiver 34 for receiving signals from the receiving and programming means 12 and output circuitry 36 which supplies stimulating pulses to the heart 38. The output of the oscillator 28 is provided to a demodulator 40, the output of which corresponds to the output of the implantable tissue stimulator VCO 16. This output is then provided to an FM detector 42 which in turn provides an output signal to a programmer and display means 44 which is proportional to the signal to be telemetered provided by the signal selection circuit 18. In addition, the programmer and display means 44 provides control signals to be telemetered to the implantable tissue stimulator 10 to a modulator 46 which modulates the oscillator 28. The output of the oscillator 28 is magnetically coupled through the programmer head 26 to the impedance reflecting circuit 14 whose output is provided to the telemetry receiver 34. In addition, the implantable stimulator 10 is powered by a battery 50 which could be of several types, two of which are a lithium iodine battery and a lithium bromine battery. The output voltage from the battery 50 is provided to the signal selection circuit 18 on an output line 51. A battery loading circuit 52 is connected to the output voltage line 51 and provides a means for selectively applying an additional load across the battery as will be explained below. Although the above description relates to a telemetry system utilizing an impedance reflecting circuit 14, the invention is in no way limited to this specific type of telemetry system and any type of telemetry system incorporated in an implantable tissue stimulator could be utilized.

Figure 2:
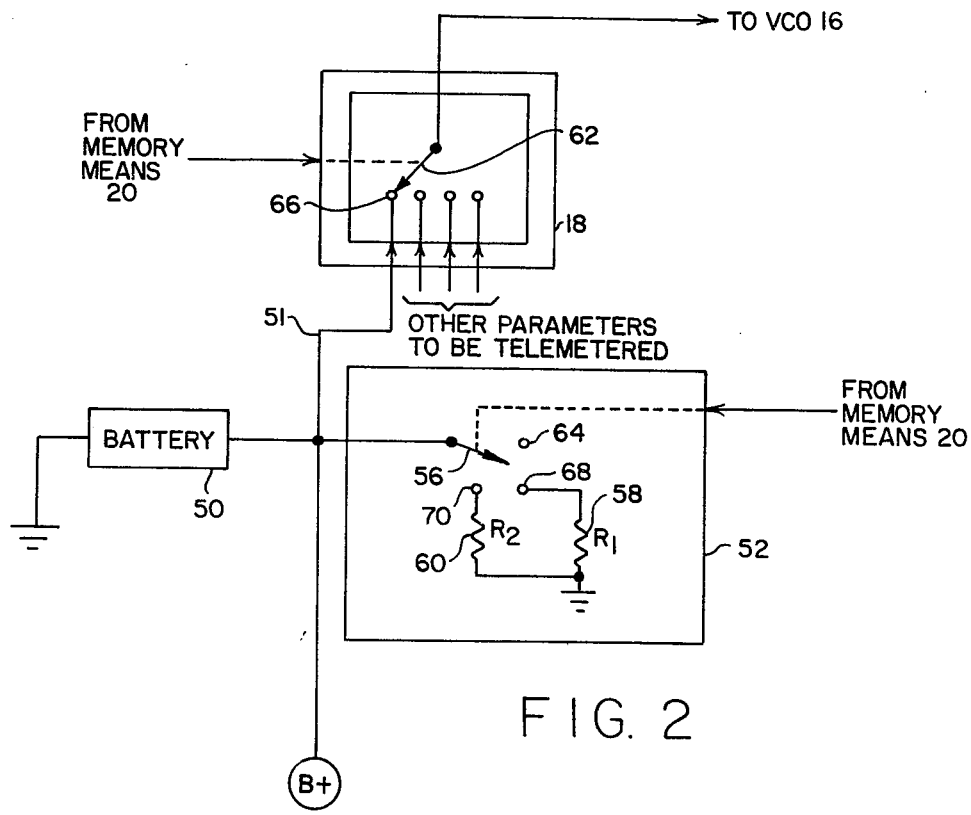
FIG. 2 is a schematic diagram showing the battery loading circuit.

Referring to FIG. 2, the battery loading circuit 52 is connected in parallel across the battery output voltage line 51 and ground, thereby not interrupting power to other portions of the tissue stimulator. The battery loading circuit 52 comprises a load switch means 56, a first loading resistor 58, and a second loading resistor 60. The signal selection circuit 18 has a signal selection switch means 62 which provides a means for connecting the battery output voltage line 51 to the VCO 16. The load switch means could be any type of electronic switch as FET switches.

In operation, the battery loading circuit 52 is normally configured so that the switch means 56 is in a first position 64 thereby unaffecting the output voltage of the battery 50. By appropriate signals, the telemetry operator through the programmer and display means 44 can cause the memory means 20 to initiate a predetermined battery impedance measuring sequence. Such a sequence comprises configuring the signal selection switch means 62 to provide the voltage appearing on a battery telemetry terminal 66 to the VCO 16. The memory means then causes the load switch means 56 to step to a second position 68 for a predetermined time period, thereby connecting the first loading resistor 58 between the battery output voltage line 51 and ground. This connection results in the battery output voltage dropping by an amount related to the internal impedance of the battery 50 as is well understood by those familiar with batteries. After a predetermined time, the memory means then causes the load switch means 56 to step to a third position 70, thereby connecting the second loading resistor 60 between the battery output voltage line 51 and ground. If the first loading resistor 58 and second loading resistor 60 have different values, then the voltage on the battery output voltage line 51 will change, thereby providing a second indication of the internal impedance of the battery 50. Although two loading resistors 58 and 60 have been illustrated, any number of loading resistors could be utilized. Although any value of load resistor could be chosen, it is preferable to choose one with a relatively high value so as to minimize current drain from the battery. Utilizing a lithium iodine battery, it has been found that values of 60,000 ohms for the first loading resistor 58 and 15,000 ohms for the second loading resistor 60 provide a satisfactory means for determining the internal impedance of the battery.

Figure 3:
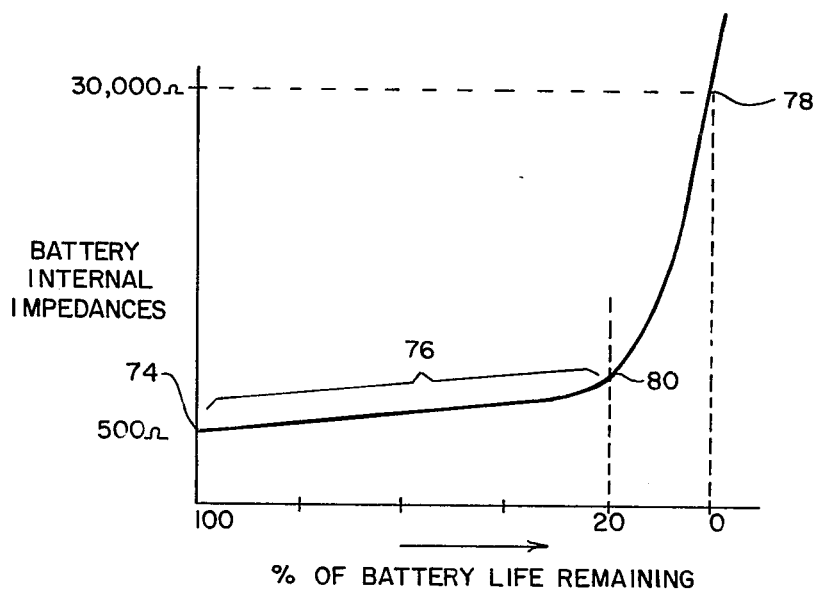
FIG. 3 is a qualitative representation of battery internal impedance as a function of the percent of battery life remaining.

A typical way in which the battery loading circuit 52 is utilized can be seen by referring to FIG. 3. However, it should be remembered that FIG. 3 is only a qualitative representation and the impedances shown do not refer to any particular battery type. Referring now to FIG. 3, a battery may have an internal impedance of 500 ohms as shown at 74. During the first 80% of battery life, the increase in internal impedance is substantially linear as shown at 76. However, when only 20 percent of the original battery life is remaining, the internal impedance increases significantly and becomes very high when the battery is exhausted as shown at 78. Thus, calculations of battery internal impedance from the telemetered voltages generated as above described provides a means for determining the life remaining in the implanted battery 50. The battery should be replaced as soon as the internal impedance begins to rise rapidly as can be seen at 80.

It should now be apparent from the above description that a battery monitoring means has been provided in which voltages related to the internal impedance of the battery are telemetered to an external receiving means, these voltages then providing a means for determining the internal impedance of the battery.

What is claimed is:

1. In an implantable living tissue stimulator powered by a battery and having a telemetry means for transmitting and receiving signals related to the operation of said tissue stimulator, a battery monitoring means comprising:
   means for providing said battery output voltage to said telemetry means;
   load means for altering current through said battery; and
   means for connecting said load means to said battery thereby altering said battery output voltage by an amount related to the internal impedance of said battery.

2. The battery monitoring means of claim 1 wherein said load means comprises at least one resistor and said means for connecting comprises switch means for connecting said at least one resistor across output terminals of said battery.

3. The battery monitoring means of claim 2 in which said at least one resistor comprises a plurality of resistors and said switch means comprises means for sequentially connecting each of said plurality of resistors across output terminals of said battery.

4. The battery monitoring means of claim 3 wherein said battery is a lithium-iodine battery and said plurality of resistors comprises a 15,000 ohm first resistor and a 60,000 ohm second resistor.

5. In an implantable living tissue stimulator powered by a battery and having a telemetry means for transmitting and receiving signals related to the operation of said tissue stimulator, a method for determining the internal impedance of said battery comprising the steps of:
   providing the battery output voltage to said telemetry means;
   connecting a load means across said battery; and
   measuring battery voltage changes resulting from said connecting step, said voltage changes being related to the internal impedance of said battery.

6. The method of claim 5 wherein said load means comprises a plurality of resistors and said connecting step further comprises the steps of sequentially connecting each of said plurality of load resistors across said battery.

* * * * *